US00PP07891P

United States Patent [19]

Zaiger et al.

[11] Patent Number: Plant 7,891

[45] Date of Patent: Jun. 23, 1992

[54] NECTARINE TREE "DESERT DELIGHT"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 629,124

[22] Filed: Dec. 14, 1990

[51] Int. Cl.[5] ..... A01H 5/00

[52] U.S. Cl. ..... Plt./41

[58] Field of Search ..... Plt./41

*Primary Examiner*—James R. Feyrer

[57] ABSTRACT

The present variety of nectarine tree has the following unique combination of desirable features:

1. Vigorous upright growth.
2. Productive and regular bearer of fruit.
3. A low chilling requirement of approximately 200 hours.
4. Fruit with attractive red skin color.
5. Fruit with good flavor and eating quality.
6. Early maturity of fruit.

1 Drawing Sheet

ORIGIN OF THE VARIETY

The new and distinct variety of nectarine tree was originated by us in the experimental orchard located near Modesto, Calif., as a first generation seedling of a cross between a selected seedling with the field identification number of 37G890 and May Glo Nectarine (U.S. Plant Pat. No. 5,245). The female parent 37G890 originated from an open pollinated seedling of Ruby Gold Nectarine (U.S. Plant Pat. No. 3,101).

ASEXUAL REPRODUCTION OF THE VARIETY

The present variety was asexually reproduced by budding, as performed by us in the experimental orchard located near Modesto, Calif., and shows that said characteristics run true to the original tree and are established and transmitted through succeeding propagations.

SUMMARY OF THE VARIETY

The herein claimed new and distinct variety of nectarine tree is of large size, vigorous upright growth and a regular and productive bearer of medium size, firm, yellow flesh, early maturing clingstone fruit, having yellow skin substantially overspread with an attractive red color. The tree is further characterized by having a low winter chilling requirement of approximately 200 hours and being a regular and productive bearer in areas with warm winter temperatures such as Palm Desert, Calif.

BRIEF DESCRIPTION OF THE PHOTOGRAPHS

The accompanying photographs show typical foliage and fruit of the present nectarine variety, with illustrations of the upper and lower surface of the foliage, an exterior view of the fruit and a fruit divided in its suture plane to reveal flesh coloration and showing a stone remaining in place. The photographic illustrations were taken shortly after being picked at maturity (firm ripe) and the colors are as nearly true as is reasonably possible in a color representation of this type.

DESCRIPTION OF THE VARIETY

The following is a detailed botanical description of the new and distinct variety of nectarine tree, its flowers, foliage and fruit as based on observations of the specimens grown near Modesto, Calif., with color terminology (except those in common terms) referenced to Reinhold color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearing.*—Regular.

Trunk:
- *Size.*—Medium stocky.
- *Surface.*—Shaggy.
- *Color.*—Brown to grayish brown.

Branches:
- *Size.*—Medium.
- *Texture.*—Medium shaggy.
- *Lenticels.*—Medium size. Medium number.
- *Color.*—Reddish brown to brown.

Leaves:
- *Size.*—Medium to large. Average length 6½" to 7". Average width 1¼" to 1½".
- *Form.*—Lanceolate, pointed.
- *Texture.*—Smooth.
- *Thickness.*—Medium.
- *Margin.*—Crenate.
- *Petiole.*—Medium length. Medium thickness.
- *Glands.*—Globose. Average number 2, range 1 to 4. Positioned on lower portion of leaf blade and upper portion of petiole.
- *Color.*—Upper surface — green to dark green (26-E-6) to (26-F-6). Lower surface — grayish green to dull green (28-D-5) to (28-E-5).

Flower buds:
- *Size.*—Medium to large.
- *Form.*—Plump.
- *Length.*—Medium.

Flowers:
- *Size.*—Large, showy.
- *Blooming period.*—Feb. 12, 1988 to Feb. 24, 1988. Varies slightly with climatic conditions.
- *Color.*—Pink.
- *Pollen.*—Present.

Fruit:
- *Maturity when described.*—Firm ripe.

*Date of first picking.*—Jun. 3, 1988.

*Date of last picking.*—Jun. 8, 1988.

*Size.*—Medium. Average diameter axially — $2\frac{1}{2}''$ to $2\frac{7}{8}''$. Average transversely in suture plane — 2 7/16" to 2 13/16".

*Form.*—Globose, only slightly elongated.

*Suture.*—Pronounced, somewhat lipped, extends from base to apex.

*Apex.*—Usually rounded to slightly retuse.

*Base.*—Retuse.

*Cavity.*—Rounded to slightly elongated in suture plane. Average depth — $\frac{1}{2}''$. Average breadth — $\frac{3}{4}''$.

Skin:

*Thickness.*—Medium.

*Texture.*—Medium — tenacious to flesh.

*Tendency to crack.*—None.

*Down.*—Wanting.

*Color.*—Yellow ground color (4-A-7) to (4-A-8). Overspread with red (10-A-8) to (10-B-8).

Flesh:

*Texture.*—Firm.

*Ripens.*—Evenly.

*Fibers.*—Few, tender.

*Juice.*—Moderate.

*Flavor.*—Mild, subacid to acid.

*Aroma.*—Moderate.

*Eating quality.*—Good.

*Color.*—Pale yellow to light yellow (3-A-3) to (3-A-5).

Stone:

*Type.*—Clingstone.

*Size.*—Large. Average length — $1\frac{3}{8}''$. Average breadth — $1\frac{1}{8}''$. Average thickness — $\frac{3}{4}''$.

*Form.*—Oval to ovate.

*Base.*—Rounded, varies from straight to rounded.

*Apex.*—Acuminate.

*Sides.*—Mostly equal.

*Surface.*—Furrowed toward apex, pitted throughout, heavier toward base.

*Tendency to split.*—Slight.

*Color.*—Tan to light brown (6-B-4) to (6-C-5).

Use: Dessert.

*Market.*—Local and long distance.

Keeping quality: Good.

Shipping quality: Good.

The present variety of nectarine tree, its flowers and fruit herein described may vary in slight detail due to variations in climate, soil conditions and cultural practices under which the variety may be grown. The above botanical description is that of the variety grown under the ecological conditions prevailing near Modesto, Calif.

We claim:

1. A new and distinct variety of nectarine tree substantially as illustrated and described, characterized by its large size, vigorous upright growth, and a regular and productive bearer of medium size, firm, yellow flesh, clingstone fruit; the tree is further characterized by having a low winter chilling requirement of approximately 200 hours and regularly bearing early maturing fruit with good flavor and eating quality in areas with warm winter climates such as Palm Desert, Calif.

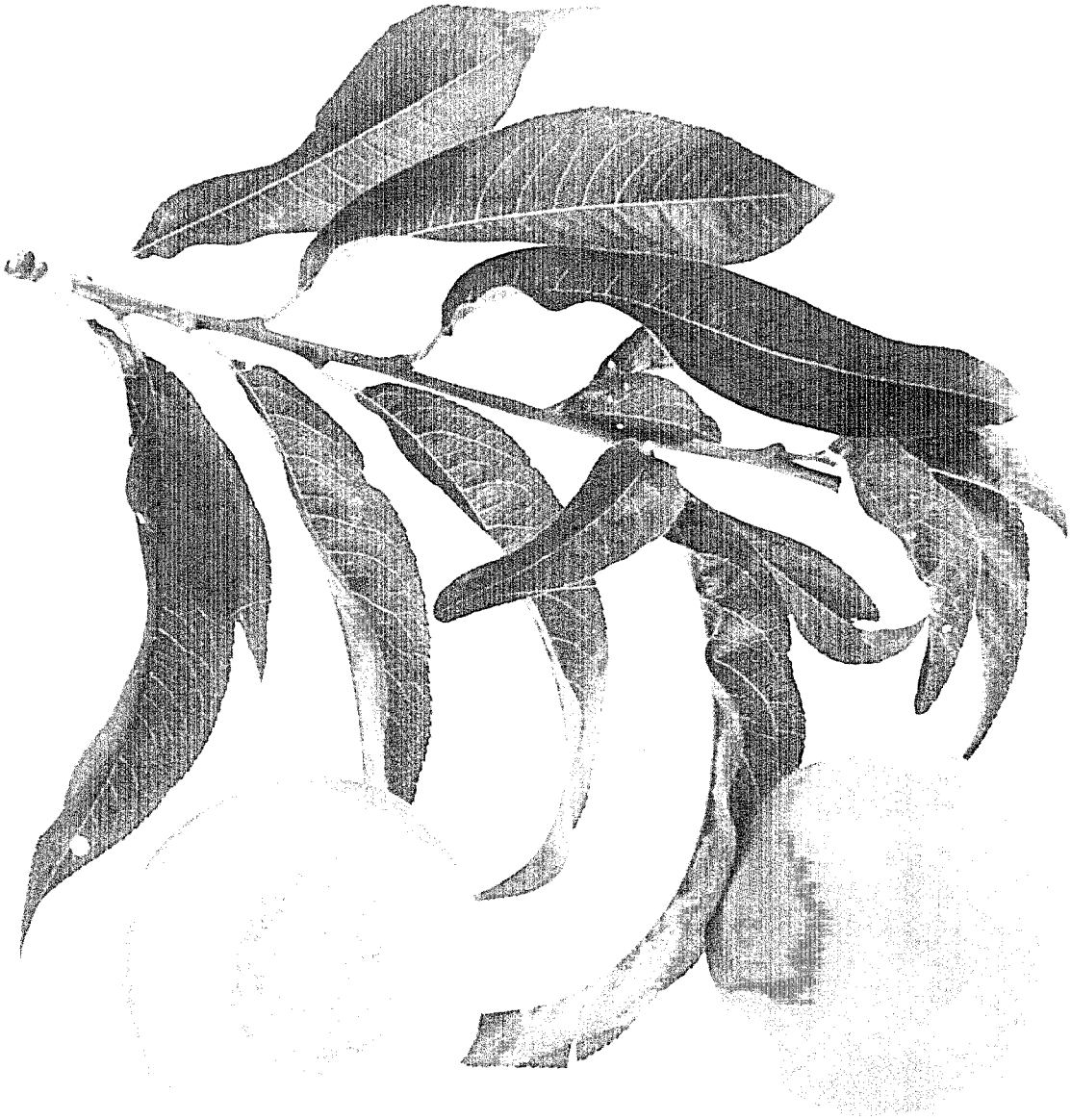

* * * * *